United States Patent [19]

Psaar

[11] Patent Number: 4,902,806
[45] Date of Patent: Feb. 20, 1990

[54] BIS(INDOLYL)ETHYLENE ALDEHYDES

[75] Inventor: Hubertus Psaar, Leverkusen, Fed. Rep. of Germany

[73] Assignee: Bayer Aktiengesellschaft, Leverkusen, Fed. Rep. of Germany

[21] Appl. No.: 261,946

[22] Filed: Oct. 24, 1988

[30] Foreign Application Priority Data

Nov. 11, 1987 [DE] Fed. Rep. of Germany ....... 3738238

[51] Int. Cl.$^4$ ............................................. C07D 403/06
[52] U.S. Cl. .................................................... 548/455
[58] Field of Search ......................................... 548/455

[56] References Cited

U.S. PATENT DOCUMENTS

| 2,154,926 | 4/1939 | Wolff et al. | 548/455 |
| 3,928,313 | 12/1975 | Papa et al. | 260/173 |
| 4,510,156 | 4/1985 | Kabbe et al. | 548/455 |

FOREIGN PATENT DOCUMENTS

| 2259883 | 8/1975 | France . | |
| 512477 | 9/1939 | United Kingdom | 548/455 |

OTHER PUBLICATIONS

*Journal of Heterocyclic Chemistry*, vol. 22, #2, Mar.-Apr. 1985, "Reactions of Indoles w/Ortho Esters, N,N-Dimethylacetamide Dialkyl Acetals", Bergman, J., pp. 341-343.

*Liebigs Annalen Der Chemie*, Heft 9, Sep. 1988, pp. 923-924, plus cover; "Form.von Vinylindo.mit Drethoxycarb.-tetra.", Camran Flo and Ulf Pindur, Apr. 22, 1988.

Primary Examiner—David B. Springer
Attorney, Agent, or Firm—Sprung Horn Kramer & Woods

[57] ABSTRACT

Bis(indolyl)ethylene aldehydes of the general formula

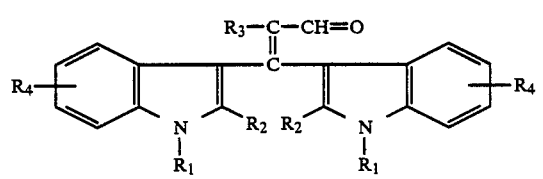

in which
$R_1$ denotes hydrogen, alkyl, aralkyl or aryl,
$R_2$ denotes hydrogen, alkyl or aryl,
$R_3$ denotes hydrogen, alkyl, alkenyl, COOH or aryl and
$R_4$ denotes hydrogen, alkyl, alkoxy, cycloalkoxy or halogen, and these substituents themselves can carry non-ionic radicals or a carboxyl group, are dyestuff intermediates.

7 Claims, No Drawings

BIS(INDOLYL)ETHYLENE ALDEHYDES

The invention relates to bis(indolyl)ethylene aldehydes of the general formula

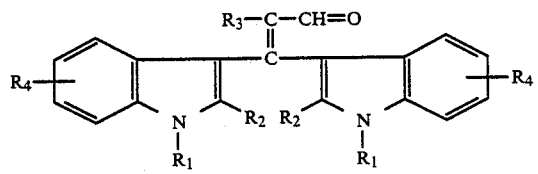     I in which
$R_1$ denotes hydrogen, alkyl, aralkyl or aryl,
$R_2$ denotes hydrogen, alkyl or aryl,
$R_3$ denotes hydrogen, alkyl, alkenyl, COOH or aryl and
$R_4$ denotes hydrogen, alkyl, alkoxy, cycloalkoxy or halogen, and
these substituents themselves can carry non-ionic radicals or a carboxyl group, and also to their preparation.

They are prepared by reaction of bis(indolyl)ethylenes of the general formula

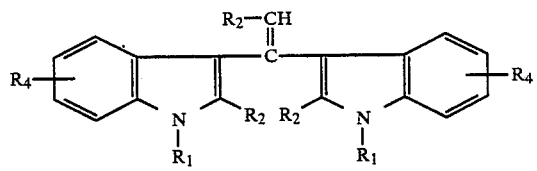     II in phosphorus oxychloride with dimethylformamide or by reaction of indoles of the general formula

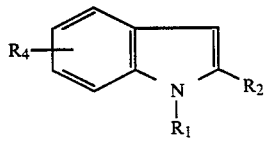     III with carboxylic acids of the general formula $R_3$—$CH_2$—COOH     IV their chlorides, esters, for example alkyl esters, or anhydrides in the presence of phosphorus oxychloride and, without isolation, by further reaction with dimethylformamide.

Preferably, alkyl stands for $C_1$–$C_{12}$-alkyl, alkoxy stands for $C_1$–$C_{12}$-alkoxy, alkenyl stands for $C_2$–$C_{12}$-alkenyl, aryl stands for phenyl, aralkyl stands for benzyl or phenylethyl, cycloalkyl stands for cyclopentyl or cyclohexyl, cycloalkoxy stands for cyclohexoxy or cyclopentoxy and halogen stands for fluorine, chlorine or bromine, in particular chlorine.

Non-ionic radicals can be, for example, halogen, in particular chlorine, $C_1$–$C_4$-alkoxy, cyano and in addition $C_1$–$C_4$-alkyl in the case of cyclic substituents.

The preferred reaction temperature of the reaction with dimethylformamide is 25° C. to 105° C., and the preferred reaction time is between 1 and 15 hours.

Dimethylformamide should be added at least in molar amounts, relative to the ethylene compound.

The reaction can be carried out in the presence or absence of solvent, the amount of phosphorus oxychloride in the latter case being such that it simultaneously acts as a solvent. The solvents used can be aromatics, alkylated aromatics or chlorinated aromatics. Suitable solvents are for example toluene, xylene, chlorobenzene or dichlorobenzene.

The molar ratio of IV:III should be at least 1:2. The preferred temperature of this reaction is 50° C. to 105° C.

Preference is given to the compounds of the formula I in which
$R_2$ is phenyl and the remaining substituents have the abovementioned meaning.

Particular preference is given to aldehydes of the formula I in which
$R_1$ denotes hydrogen, alkyl or benzyl, which can be substituted by alkyl, alkoxy or halogen,
$R_2$ denotes phenyl or phenyl substituted by alkyl, alkoxy or halogen,
$R_3$ denotes hydrogen, alkyl or phenyl and
$R_4$ denotes hydrogen, alkyl, alkoxy or halogen,
and in which alkyl stands for $C_1$–$C_{12}$-alkyl and alkoxy stands for $C_1$–$C_{12}$-alkoxy and the alkyl radicals can be substituted by chlorine, cyano or carboxyl.

The compounds of the formula I are useful intermediates for dyestuffs and for colour formers which are described, for example, in DE-A 3,738,240.

EXAMPLE 1

3.5 parts by weight of phosphorus oxychloride are added to 30 parts by weight of dimethylformamide, and 6.2 parts by weight of 1,1-bis(1,2-dimethylindolyl)ethylene are added to this mixture at 50° C. The batch is stirred at 50° C. for 2 hours, then discharged into 500 parts by weight of icewater, and made alkaline with 10% strength sodium hydroxide solution. The aldehyde is filtered off with suction and dried in vacuo at 50° C.

Yield: 5.4 parts by weight, m.p.: 208° C.

The compound has the formula

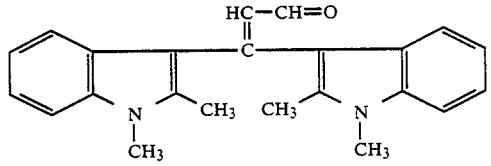

EXAMPLE 2

20.7 parts by weight of 1-methyl-2-phenylindole are heated in 30 ml of phosphorus oxychloride to 80° to 90° C. with stirring. At this temperature 12 parts by weight of acetic anhydride are added dropwise, and the batch is stirred at 100° C. for 30 minutes. 4.0 parts by weight of dimethylformamide are then added, and the batch is stirred at 90° C. for another hour. After cooling to room temperature, the mixture is poured into 700 parts by weight of water and the mixture is stirred for 20 hours until crystallization occurs. The aldehyde is filtered off with suction, washed with water and dried in vacuo at 50° C. The compound is recrystallized from methanol with the addition of activated carbon.

The yield is 23.9 parts by weight, m.p.: 227° C.

The compound has the formula

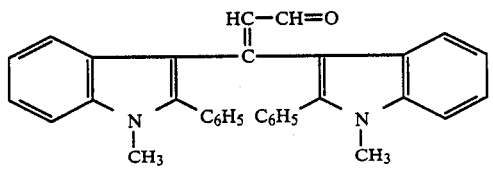

EXAMPLE 3

23.7 parts by weight of 1-methyl-2-(4-methoxyphenyl)-indole are heated in 50 ml of phosphorus oxychloride to 90° C., and 3.7 parts by weight of propionic acid are added dropwise at this temperature. After 30 minutes, the mixture is cooled to room temperature, and 100 ml of methanol are slowly added. 3.8 parts by weight of dimethylformamide are then added to the batch, which is stirred at 90° C. for 1 hour.

The batch is poured into 500 parts by weight of water and brought to a pH of 10 with sodium hydroxide solution. The product is filtered off with suction and dried in vacuo at 50° C.

Yield: 24.2 parts by weight, m.p.: 205° C.

The compound has the formula

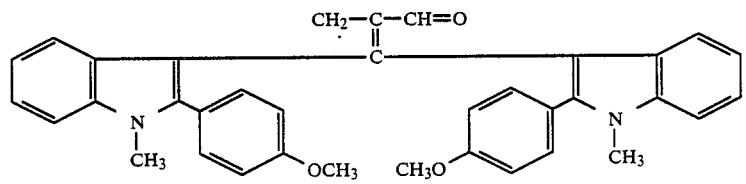

According to Examples 1 to 3, the following aldehydes of the formula

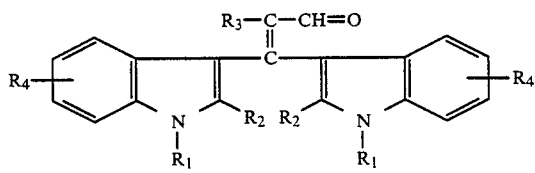

were prepared:

I claim:

1. A bis(indolyl) ethylene aldehyde of the formula

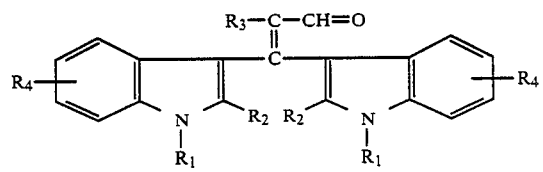

in which $R_1$ denotes hydrogen, $C_1$-$C_{12}$-alkyl, aralkyl, wherein said aralkyl is benzyl or phenylethyl or phenyl, $R_2$ denotes hydrogen, $C_1$-$C_{12}$-alkyl or phenyl, $R_3$ denotes hydrogen, $C_1$-$C_{12}$-alkyl, $C_2$-$C_{12}$-alkenyl, COOH or phenyl and $R_4$ denotes hydrogen, $C_1$-$C_{12}$-alkyl, $C_1$-$C_{12}$-alkoxy, cycloalkoxy or halogen, said alkyl being unsubstituted or substituted by a halogen, $C_1$-$C_4$-alkoxy cyano or a carboxyl group, said aralkyl being unsubstituted or substituted by halogen, cyano, $C_1$-$C_4$-alkoxy or a carboxyl group, said phenyl being unsubstituted or substituted by a halogen, $C_1$-$C_4$-alkoxy, cyano, $C_1$-$C_4$-alkyl or a carboxyl group, said alkoxy being unsubstituted or substituted by a halogen, cyano or a carboxyl group, said cycloalkoxy being unsubstituted or substituted by a halogen, cyano or a carboxyl group.

2. A bis(indolyl) ethylene aldehyde according to claim 1, wherein $R_2$ stands for phenyl.

3. A bis(indolyl ethylene aldehyde according to claim 1, wherein $R_1$ denotes hydrogen, $C_1$-$C_{12}$-alkyl or benzyl, which is unsubstituted or substituted by $C_1$-$C_{12}$-alkyl, $C_1$-$C_{12}$-alkoxy or halogen,

| Example | $R_1$ | $R_2$ | $R_3$ | $R_4$ | F. |
|---|---|---|---|---|---|
| 4 | $C_2H_4CN$ | $C_6H_5$ | H | H | 172° C. |
| 5 | H | $C_6H_5$ | H | H | 204° C. |
| 6 | $CH_3$ | $CH_3$ | H | H | 208° C. |
| 7 | $CH_3$ | H | H | H | 193–195° C. |
| 8 | $CH_3$ | $CH_3$ | $CH_3$ | H | 192° C. |
| 9 | $C_4H_9$ | $CH_3$ | H | H | 1 |
| 10 | $CH_3$ | $CH_3$ | $C_{10}H_{21}$ | H | 1 |
| 11 | $C_2H_4COOH$ | $C_6H_5$ | H | H | >300° C. |
| 12 | $C_2H_9$ | $C_6H_5$ | H | H | 114° C. |
| 13 | $C_6H_5CH_2$ | $C_6H_5$ | H | H | 195° C. |
| 14 | $C_6H_5CH_2$ | $CH_3$ | H | H | 145° C. |
| 15 | $CH_3$ | $C_6H_5$ | H | H | >325° C. |
| 16 | $CH_3$ | $C_6H_5$ | $C_2H_4Cl$ | H | 178° C. |
| 17 | $CH_3$ | $C_6H_4$, 4-$OCH_3$ | H | H | 130° C. |
| 18 | $CH_3$ | $C_6H_4$, 4-Cl | H | H | 213–215° C. |
| 19 | $CH_3$ | $C_6H_5$ | $CH_2$=$CH_2$ | H | 165–167° C. |
| 20 | $CH_3$ | $C_6H_5$ | H | 6-Cl | 229° C. |
| 21 | $CH_3$ | $C_6H_5$ | H | 5-$CH_3$ | 177° C. |
| 22 | $C_2H_5$ | $C_6H_5$ | H | H | 181–183° C. |
| 23 | $CH_3$ | $CH_2$—$CH(CH_3)_2$ | H | H | 1 |

$R_2$ denotes phenyl or phenyl substituted by $C_1$–$C_4$-alkyl, $C_1$–$C_4$-alkoxy or halogen, $R_3$ denotes hydrogen, $C_1$–$C_{12}$-alkyl or phenyl and $R_4$ denotes hydrogen, $C_1$–$C_{12}$-alkyl, $C_1$–$C_{12}$-alkoxy or halogen, the alkyl radicals being unsubstituted or substituted by chlorine, cyano or carboxyl.

4. A bis(indolyl)ethylene aldehyde according to claim 1, wherein said halogen is fluorine, chlorine or bromine.

5. A bis(indolyl)ethylene aldehyde according to claim 1, wherein said halogen is chlorine.

6. A bis(indolyl)ethylene aldehyde according to claim 1, wherein said phenyl is substituted with chlorine or —$OCH_3$.

7. A bis(indolyl)ethylene aldehyde according to claim 1, wherein said cycloalkoxy is cyclohexoxy or cyclopentoxy.

* * * * *